United States Patent [19]
Kim et al.

[11] Patent Number: 5,491,251
[45] Date of Patent: Feb. 13, 1996

[54] 2-BENZOYL-3-AMINOACRYLATE DERIVATIVES AND METHODS FOR THE PREPARATION OF THE SAME

[75] Inventors: You Seung Kim; Soon Bang Kang; Seon Hee Park, all of Seoul, Rep. of Korea

[73] Assignee: Korea Institute of Science and Technology, Seoul, Rep. of Korea

[21] Appl. No.: 321,370

[22] Filed: Oct. 11, 1994

[30]   Foreign Application Priority Data

Mar. 24, 1994 [KR]   Rep. of Korea ............... 1994/5974

[51] Int. Cl.⁶ .................. C07C 205/06; C07C 229/30
[52] U.S. Cl. ................................. 560/23; 560/37
[58] Field of Search ......................... 560/23, 37

[56]           References Cited

FOREIGN PATENT DOCUMENTS 3543513   6/1987   Germany .

OTHER PUBLICATIONS

Chemical Abstract 154342 107:704 (1987).
Mitscher, et al., "Chiral DNA Gyrase Inhibitors. 2. Asymmetric Synthesis and Biological Activity of the Enantiomers of 9–Fluoro–3–methyl–10–(4–methyl–1–piperazinyl)–7–oxo–2,3–dihydro–7H–pyrido[1,2,3–de]–1,4–benzoxazine–6–carboxylic Acid (Ofloxacin)", *J. Med. Chem.*, 30:2283 (1987).
Hayakawa, et al., "Synthesis an antibacterial Activities of Substituted 7–Oxo–2,3–dihydro–7H–pyrido–[1,2,3,–de][1,4] benzoxazine–6–carboxylic Acids", *Chem. Pharm. Bull.*, 32:4907–4913 (1984).

*Primary Examiner*—José G. Dees
*Assistant Examiner*—Joseph M. Conrad, III
*Attorney, Agent, or Firm*—Townsend and Townsend and Crew

[57]           ABSTRACT

2-benzoyl-3-aminoacrylate derivatives of the following formula I and methods for the preparation of the same.

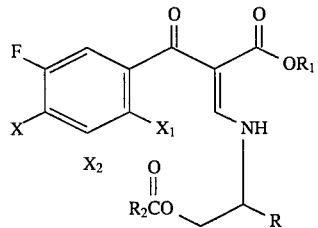

wherein X is a halogen; $X_1$ and $X_2$ are independently selected from a halogen and a nitro; and R, $R_1$ and $R_2$ each is an alkyl group containing 1 to 4 carbon atoms. The compounds can be used as starting materials to synthesize benzoxazine derivatives, potent antibacterial compounds.

1 Claim, No Drawings

2-BENZOYL-3-AMINOACRYLATE DERIVATIVES AND METHODS FOR THE PREPARATION OF THE SAME

BACKGROUND OF THE INVENTION 1. Field of the Invention

The present invention relates to a novel compound useful for preparing antibacterial benzoxazine derivatives. More particularly, the present invention relates to 2-benzoyl-3-aminoacrylate derivatives represented by the following general formula I and the method for preparing the same.

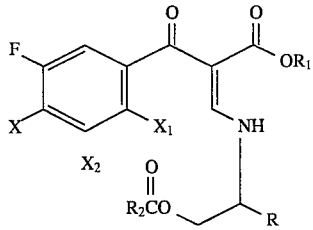

wherein

X is a halogen;

$X_1$ and $X_2$ are independently selected from a halogen and a nitro; and

R, $R_1$ and $R_2$ each is an alkyl group containing 1 to 4 carbon atoms.

The compound of formula I of the present invention can be used as a starting material for preparing antibacterially active benzoxazine derivatives of the following formula VIII which in turn serves as an intermediate for synthesizing a potent antibacterial compound ofloxacin (*Chem. Pharm. Bull*, 32, 4907–4913 (1984)):

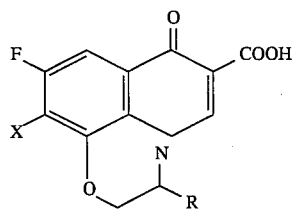

wherein X and R are as defined hereinabove.

Further, in Korean Patent Application No. 94-5975 to the present inventors, applied on Mar. 24, 1994, an improved method for the preparation of the aforementioned compound of formula VIII was suggested, using the subject compound of formula I.

2. Description of the Prior Art

Conventionally, there has been provided a compound of formula 3 as an intermediate for the preparation of the benzoxazine derivatives. However, it needs many steps to obtain the compound of formula 3 such as reacting 2, 3, 4, 5-tetrafluoro benzoyl chloride 1 with ethyl ethoxymagnesium malonate and further reacting the resulted ethyl (2,3, 4,5-tetrafluorobenzoyl)acetate 2 with triethyl orthoformate/ acetic anhydride and then substituting the obtained compound with 2-amino-1-propanol to obtain the compound of formula (see M. Schriewer, K. Grohe, H. J. Zeiler and K. G. Hetzger, German Offen. DE 3,543,513 (1987); Chem. Abstr., 107, 154342c (1987); L. A. Mitscher, P. N. Sharma, D. T. W. Chu., L. L. Shen and A. G. Pernet, *J. Med. Chem.* 30, 2283 (1987)). Further, it is another problem of the obtained compound of formula 3 being not sufficiently stable and difficulty of handling thereof.

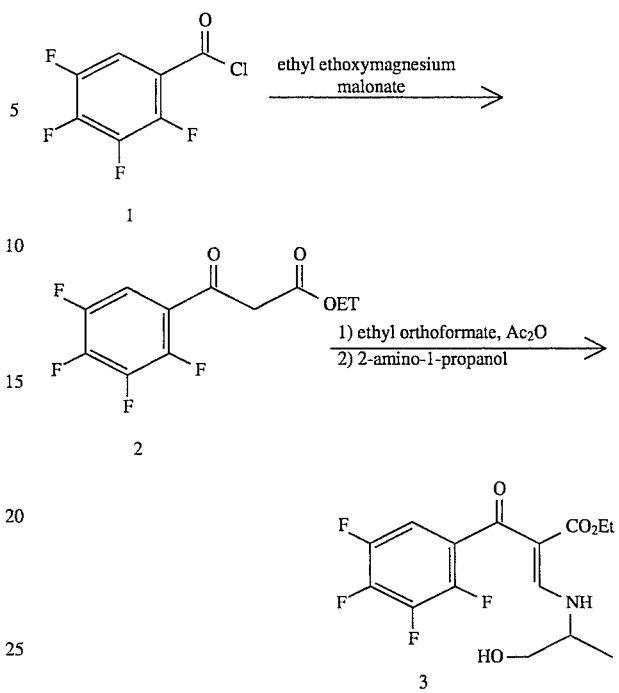

SUMMARY OF THE INVENTION

In view of the foregoing, it is an object of the present invention to provide novel starting materials, 2-benzoyl-3-aminoacrylate derivatives of the general formula I, useful to synthesize antibacterially active benzoxazine carboxylic acids derivatives.

It is an another object of the present invention to provide a method for preparing 2-benzoyl-3-aminoacrylate derivatives of formula I.

It is also an object of the present invention to provide novel acrylate derivatives of formula IV and alkyl acrylate derivatives of formula VI.

$$R_2CO\text{-}\underset{R}{CH}\text{-}NHCH=CHCO_2R_1 \quad\quad VI$$

wherein, R, $R_1$, and $R_2$ are as defined hereinabove.

The compound of formula I of the present invention is much more stable than the conventional compound of formula 3, and easy to handle.

DETAILED DESCRIPTION OF THE INVENTION

The compounds of formula I can be obtained by reacting alkylpropiolate of the following general formula II $$HC\equiv CCO_2R_1 \quad\quad II$$

wherein $R_1$ is an alkyl group containing 1 to 4 carbon atoms, with a compound of the following general formula III $$HO\text{-}\underset{R}{CH}\text{-}NH_2 \quad\quad III$$

wherein R is an alkyl group containing 1 to 4 carbon atoms, in the presence of an organic solvent, to give a novel acrylate derivative of the following general formula IV

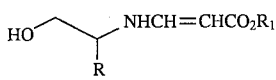  IV wherein R and $R_1$ are alkyl group containing 1 to 4 carbon atoms; treating the novel acrylate derivative of formula IV with an acyl chloride derivative of the following general formula V

  V wherein $R_2$ is an alkyl group containing 1 to 4 carbon atoms, to give a novel alkylacrylate derivative of the following general formula VI

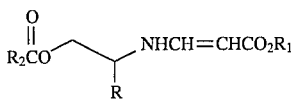  VI wherein R, $R_1$ and $R_2$ are as defined hereinabove; and treating the novel alkylacrylate derivative of formula VI with a benzoyl chloride derivative of the following general formula VII

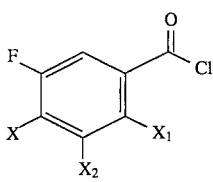  VII wherein X is a halogen; and $X_1$ and $X_2$ are independently selected from a halogen and a nitro, in the presence of a suitable base.

In order to help understand the present invention, the preparation method of the present invention is summarized in the following scheme.

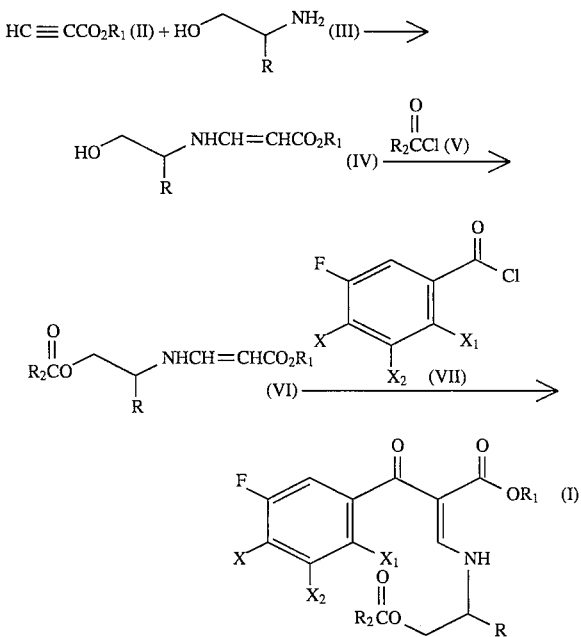

In accordance with a further aspect of the present invention, there is provided a novel compound of formula IV, an intermediate useful to prepare the compound of formula I.

In accordance with still a further aspect of the present invention, there is provided a novel compound of formula VI, another intermediate useful to prepare the compound of formula I.

As for an organic solvent effective for the reaction of the compound of formula II with the compound of formula III, acetonitrile, tetrahydrofuran, dimethylformamide, dioxane, dimethylacetamide, dimethylsulfoxide, chloroform, methylenechloride, ethylenechloride or diethylether is used. In the presence of the organic solvent, this reaction is carried out at a reaction temperature of 0 to 25° C. for 1 to 10 hours. In the reaction, the equivalent ratio of the compound of formula II to the compound of formula III is preferably 1:1.

Preferred base for the treatment of the compound of formula IV with the compound of formula V include triethylamine, pyridine, potassium carbonate, sodium carbonate, calcium carbonate, 4-dimethylaminopyridine, 1,8-diazabicyclo[5.4.0]undec-7-en] or 1,5-diazabicyclo[4.3.0]non-5-en. In an organic solvent, such as methylenechloride, ethylenechloride, diethylether, chloroform, acetonitrile or tetrahydrofuran, the compound of formula IV is stirred along with the compound of formula V in the presence of the above-mentioned base, so as to give an alkylacrylate derivative of formula VI, a novel compound. When carrying out this reaction, the equivalent ratio of the compound of formula IV to the compound of formula V to the base is preferably in the range of 1:1.1:1.1 to 1:1.1:1.5.

While being heated, the alkylacrylate derivative of formula VI is stirred along with a benzoyl chloride derivative of formula VII in an organic polar solvent, such as methylenechloride, ethylenechloride, diethylether, chloroform, acetonitrile and tetrahydrofuran, at between 0 and 100° C. for 10 minutes to 2 hours in the presence of base, so as to yield 2-benzoyl-3-aminoacrylate derivatives of formula I. As for the base, triethylamine, pyridine, potassium carbonate, sodium carbonate, calcium carbonate, 4-dimethylaminopyridine, 1,8-diazabicyclo[5.4.0] undec-7-en or 1,5-diazabicyclo-[4.3.0]non-5-en may be used. In this reaction, the equivalent ratio of the compound of formula VI to the compound of formula VII to the base is preferably in the range of 1:1.1:1.2 to 1:1.2:1.5.

The products can be separated and purified by conventional techniques, such as evaporation, filtration, extraction, chromatography, distillation and the combinations thereof. For example, the mixture of reactants is initially dried under reduced pressure to condense it. The resultant residual matter is added in a mixture of an organic solvent, such as methylenechloride, chloroform, diethylether or ethylacetate, and water and then stirred. Thereafter, the organic solvent is condensed to leave a product. In case of a mixture of product and by-products, further purification may be performed by chromatography, re-distillation or recrystallization.

The preferred embodiments of the present invention will now be further described with reference to specific examples. Unless otherwise stated all percentage, part and ratio therein are by weight.

Example 1

Ethyl 3-[(1-hydroxyprop-2-yl)amino]acrylate (IV: R=methyl, $R_1$=ethyl)

7.52 g (0.1 mol) of 2-amino-1-propanol (III: R=methyl) was added in 150 ml of acetonitrile and cooled to 0° C. To this, 9.82 g (0.1 mol) of ethyl propiolate (II, $R_1$=ethyl) was slowly added dropwise. The reactant mixture was stirred at not more than 5° C. for 8 hours and further stirred at room temperature for 1 hour.

After completion of the reaction, the solvent was removed under reduced pressure (25° C./5 mmHg), to give 17.2 g of colorless oily product (yield 99%).

Analysis of the product revealed that Z and E isomers were present in a ratio of 6:4 therein.

IR (KBr) cm$^{-1}$: 3340, 1662

NMR(CDCl$_3$) ppm: 7.74–7.92(1Hx3/5, m), 7.48(1Hx2/5, dd, J=10, 13H), 6.73(1Hx3/5, dd, J=13H), 4.82–4.95(1Hx2/5, m), 4.76(1Hx2/5, d, J=13H), 4.49(1Hx3/5, d, J=8H), 4.10(2Hx2/5, q, J=7H), 4.09(2Hx3/5, q, J=7H), 3.41–3.69(2H, m), 3.28–3.37(1H, m), 2.20–2.40(1H, brs), 1.25(3Hx3/5, t, J=7H), 1.24(3Hx2/5, t, J=7H), 1.19(3Hx3/5, d, J=6.6H), 1.18(3Hx2/5, d, J=6.4H)

Example 2

Ethyl 3-[(1-hydroxyprop-2-yl)amino]acrylate ( IV: R=methyl, R$_1$=ethyl)

3.76 g (50 mmol) of 2-amino-1-propanol (III: R=methyl) was added to 100 ml of dimethylformamide and cooled. To this, 4.91 g (50 mmol) of ethyl propiolate (II, R$_1$=ethyl) was slowly added dropwise. The reactant mixture was stirred at not more than 5° C. for 6 hours and further stirred at room temperature for 2 hour.

After completion of the reaction, the mixture was subjected to purification in the same manner as that of Example 1, to give 7.96 g of colorless oily product (92% yield).

Example 3

Ethyl 3-[(1-acetoxyprop-2-yl)amino]acrylate (VI: R, R$_2$=methyl, R$_1$=ethyl)

6.92 g (40 mmol) of ethyl 3-[(1-hydoxyprop-2 yl)amino] acrylate (IV: R=methyl, R$_1$=ethyl), 6.42 ml (46 mmol) of triethylamine and 0.48 g (4 mmol) of 4-dimethylaminopyridine were added to 100 ml of methylenechloride and cooled to 0° C. To this solution, 3.02 ml (44 mmol) of acetylchloride (V, R$_2$=methyl) was slowly added dropwise. The reactant mixture was stirred for 30 minutes at 5° C. and then, precipitate was filtered off.

Thereafter, the remaining filtered solution was washed with 20 ml of aqueous 0.2N hydrochloric acid solution, 10 ml of saturated aqueous sodium bicarbonate solution, and 10 ml of saturated saline water, in due order and then the organic solvent was dried over magnesium sulfate. Thereafter, the organic solvent was completely removed under reduced pressure (25° C./20 mmHg), to give 8.46 g of an oily product (98% yield).

Analysis of the product revealed that Z and E isomers were present in a ratio of 6:4 therein.

b.p.: 70°–80° C./1.6 mmHg

IR (NaCl) cm$^{-1}$: 3330, 1741, 1667

NMR(CDCl$_3$) ppm: 7.69–7.87(1Hx3/5, m), 7.44(1Hx2/5, dd, J=13, 9H), 6.67(1Hx3/5, dd, J=13, 8H), 4.85–4.95(1Hx2/5, m), 4.79(1Hx2/5, d, J=13H), 4.50(1Hx3/5, d, J=8H), 4.11(2H, q, J=7H), 3.95–4.06(2H, m), 3.38–3.69(1H, m), 2.08(3H, s), 1.26(3H, t, J=7H)

Analysis for C$_{10}$H$_{17}$O$_4$N$_1$ Calculated: C; 55.80, H; 7.96, N; 6.51 Found: C; 55.62, H; 7.92, N; 6.39

Example 4

Ethyl 3-[(1-acetoxyprop-2-yl)amino]acrylate (VI: R, R$_2$=methyl, R$_1$=ethyl)

3.46 g (20 mmol) of ethyl 3-[(1-hydoxyprop-2-yl)amino] acrylate (IV: R=methyl, R$_1$=ethyl), 1.9 g (24 mmol) of pyridine were added to 50 ml of acetonitrile and cooled to 0° C. To this solution, 1.51 ml (22 mmol) of acetylchloride (V, R$_2$=methyl) was slowly added dropwise. The reactant mixture was stirred for 1 hour at 5° C. and then, precipitate was filtered off.

Thereafter, the remaining filtered solution was dried under reduced pressure (25° C./10 mmHg), to leave residue, to which 100 ml of methylenechloride was subsequently poured. This resulting mixture was washed with 10 ml of aqueous 0.2N hydrochloric acid solution, 10 ml of aqueous sodium bicarbonate solution, and 10 ml of saturated saline water, in due order and then organic solvent was dried over magnesium sulfate. Thereafter, the organic solvent was completely removed under reduced pressure (25° C./20 mmHg), to give 3.87 g of an oily product (90% yield).

Example 5

Ethyl 2-(2-nitro-3,4,5-trifluoro)benzoyl-3-[(1-acetoxyprop-2-yl)amino] acrylate (I: R, R$_2$=methyl, R$_1$=ethyl, X, X$_2$=fluoro, X$_1$=nitro)

4.305 g (20 mmol) of ethyl 3-[(1-acetoxyprop-2-yl)amino]acrylate (VI: R, R$_2$=methyl, R$_1$=ethyl) and 3.07 ml (22 mmol) of triethylamine were added to 170 ml of acetonitrile and cooled to 0° C. To this solution, 5.03 g (21 mmol) of 2-nitro-3,4,5-trifluorobenzoyl chloride (VII: X, X$_2$=fluoro, X$_1$=nitro) was slowly added dropwise. This reactant mixture was stirred for 30 minutes with heating and cooled to room temperature. Precipitate was filtered off.

Thereafter, the remaining filtered solution was dried under reduced pressure (25° C./10 mmHg), to leave residue, to which 200 ml of methylenechloride was subsequently poured. This resulting mixture was washed with 20 ml of saturated aqueous ammonium chloride solution, 20 ml of saturated aqueous sodium bicarbonate solution, and 20 ml of saturated saline water, in due order and then the organic solvent was dried over magnesium sulfate. Thereafter, the organic solvent was completely removed under reduced pressure (25° C./20 mmHg), to give 8.28 g of an oily product (99% yield).

Analysis of the product revealed that two isomers were present at the ratio of 4:1 therein.

b.p.: 150°–160° C./1.2 mmHg IR (KBr) cm$^{-1}$: 1743, 1691, 1630, 1552 NMR(CDCl$_3$) ppm: 9.59–9.68, 10.78–10.84(1H, br), 8.26 (1Hx1/5, d, J=14H), 8.18(1Hx4/5, d, J=14H), 6.91–6.99(1H, m), 4.03(2H, q, J=7H), 3.94–4.27(2H, m), 3.78–3.86(1H, m), 2.13(3H, s), 1.43(3H, d), 1.12(3Hx4/5, t, J=7H), 0.93(3Hx1/5, t, J=7H)

Analysis for C$_{17}$H$_{17}$F$_3$N$_2$O$_7$ Calculated: C; 44.81, H; 4.10, N; 6.70 Found: C; 44.69, H; 4.08, N; 6.59

Example 6

Ethyl 2-(2-nitro-3,4,5-trifluoro)benzoyl-3-{(1-acetoxyprop-2-yl)amino] acrylate (I: R, R$_2$=methyl, R$_1$=ethyl, X, X$_2$=fluoro, X$_1$=nitro)

2.15 g (10 mmol) of ethyl 3-[(1-acetoxyprop-2-yl)amino] acrylate (VI: R, R$_2$=methyl, R$_1$=ethyl) and 1.45 g (15 mmol) of pyridine were added to 150 ml of methylenechloride and cooled. To this solution, 2.87 g (12 mmol) of 2-nitro-3,4,5-trifluorobenzoyl chloride (VII: X, X$_2$=fluoro, X$_1$=nitro) was slowly added dropwise. This reactant mixture was stirred for 2 hours with heating and then, precipitate was filtered off.

Purification procedure was carried out in the same manner as that of Example 5, to give 3.89 g of an oily product (93% yield).

Example 7

Ethyl 2-(2,3,4,5-tetrafluoro)benzoyl-3-[(1-acetoxyprop-2-yl) amino]acrylate (I: R, R$_2$=methyl, R$_1$=ethyl, X, X$_1$, X$_2$=fluoro)

2.15 g (10 mmol) of ethyl 3-[(1-acetoxyprop-2-yl)amino] acrylate (VI: R, R$_2$=methyl, R$_1$=ethyl) and 1.5 ml (11 mmol) of triethylamine were added to 80 ml of acetonitrile and cooled to 0° C. To this solution, 2.23 g (10.5 mmol) of 2,3,4,5-tetrafluorobenzoyl chloride (VII, X, X$_1$, X$_2$=fluoro) was slowly added dropwise. The reactant mixture was stirred for 30 minutes with heating and cooled to room temperature. Precipitate was filtered off.

Thereafter, the solvent was removed under reduced pressure (25° C./20 mmHg), to leave residue which was subsequently added in 50 ml of methylenechloride and washed with 10 ml of saturated aqueous ammonium chloride solution, 10 ml of saturated aqueous sodium bicarbonate solution, 10 ml of water and 10 ml of saline water, in due order.

The solvent was dried over magnesium sulfate and removed completely under reduced pressure (25° C./10 mmHg), to give 3.82 g of an oily product (97% yield). This oily product could be crystallized in-ethanol.

m.p. (EtOH): 70–71° C. IR (NaCl) cm$^{-1}$: 3279, 1745, 1698, 1632, 1571 NMR(CDCl$_3$) ppm: 9.39–10.95(1H, brs), 8.16(1Hx1/4, d, J=14.3H), 8.13(1 Hx3/4, J=13.9H), 7.08–7.16(1Hx1/4, m), 6.96–7.04(1Hx3/4, m), 4.04–4.24(2H, m), 4.04–4.08(2H, m), 3.74–3.88(1H, m), 2.13(3H, s), 1.42(3Hx3/4, d=6.81H), 1.39(3Hx1/4, d=6.81H), 1.11(3Hx3/4, t, J=7.07H), 0.98(3Hx1/4, t, J=7.14H)

Analysis for C$_{17}$H$_{17}$F$_4$N$_1$O$_5$ Calculated: C; 52.18, H; 4.38, N; 3.58 Found: C; 52.10, H; 4.35, N; 3.50

Example 8

Ethyl 2-(2,3,4,5-tetrafluoro)benzoyl-3-[(1-acetoxyprop-2-yl) amino]acrylate (I: R, R$_2$=methyl, R$_1$=ethyl, X,X$_1$,X$_2$=fluoro)

2.15 g (10 mmol) of ethyl 3-[(1-acetoxyprop-2-yl)amino] acrylate (VI: R, R$_2$=methyl, R$_1$=ethyl) and 1.45 g (15 mmol) of pyridine were added to 100 ml of tetrahydrofuran and cooled. To this solution, 2.55 g (12 mmol) of 2,3,4,5-tetrafluorobenzoyl chloride (VII, X, X$_1$, X$_2$=fluoro) was slowly added dropwise. The reactant mixture was stirred for 1 hour with heating and cooled to room temperature. Precipitate was filtered off.

Thereafter, the solvent was removed under reduced pressure(25° C./10 mmHg), to leave residue which was subsequently added in 50 ml of methylenechloride. Purification procedure was carried out in the same manner as that of Example 7, to give 3.71 g of a solid product (95% yield).

Other features, advantages and embodiments of the invention disclosed herein will be readily apparent to those of ordinary skilled in the art to which the present invention pertains after reading the foregoing disclosures. In this regard, while specific embodiments of the invention have been described, variations and modifications of these embodiments can be effected without departing from the spirit and scope of the invention as described and claimed.

What is claimed is:

1. A 2-benzoyl-3-aminoacrylate derivative having the following formula I:

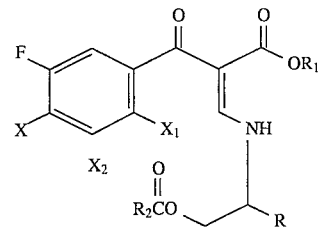

wherein
 X is a halogen;
 X$_1$ and X$_2$ are independently selected from a halogen and a nitro; and
 R, R$_1$ and R$_2$ each is an alkyl group containing 1 to 4 carbon atoms.

* * * * *